United States Patent [19]
Gatts

[11] 3,993,042
[45] *Nov. 23, 1976

[54] INFANT ENVIRONMENTAL TRANSITION SYSTEM

[76] Inventor: James D. Gatts, 4625 E. Louisiana, No. 201, Denver, Colo. 80222

[ * ] Notice: The portion of the term of this patent subsequent to May 7, 1991, has been disclaimed.

[22] Filed: May 2, 1974

[21] Appl. No.: 466,136

Related U.S. Application Data
[63] Continuation of Ser. No. 131,126, April 5, 1971, Pat. No. 3,809,065.

[52] U.S. Cl. ................................... 128/1 B; 5/61
[51] Int. Cl.² ......................................... A61B 19/00
[58] Field of Search .......... 128/1 R, 1 B, 1 C, 24 R, 128/28; 5/61, 62

[56] References Cited
UNITED STATES PATENTS

| | | | |
|---|---|---|---|
| 1,943,888 | 1/1934 | Ewald | 5/62 X |
| 2,534,471 | 12/1950 | Norheim | 5/61 |
| 2,543,426 | 2/1951 | Terhaar | 128/1 B |
| 2,723,660 | 11/1955 | Greenberg | 128/1 R |
| 2,869,538 | 1/1959 | Hawk | 128/28 |
| 3,453,999 | 7/1969 | Neal | 128/1 R X |
| 3,809,065 | 5/1974 | Gatts | 128/1 R |

FOREIGN PATENTS OR APPLICATIONS

| | | | |
|---|---|---|---|
| 255,790 | 11/1962 | Australia | 128/1 C |
| 164,040 | 9/1949 | Austria | 128/1 R |

*Primary Examiner*—Dalton L. Truluck

[57] ABSTRACT

The disclosed infant environmental transition system relates to the method and apparatus for providing an infant with an incrementally controlled, healthy transition from its intrauterine environment as it exists near birth to the extrauterine environment. The apparatus comprises a housing within which the infant is supported on a sling-like member. Means are provided to initially generate environmental conditions within the housing simulating the intrauterine environment and to alter this environment in controlled incremental steps to a normal extrauterine environment. Said means provide and control the tactile sensations perceived by the infant; the temperature and humidity within the container; the degree of movement imparted to the housing, which in turn is imparted to the infant; the degree of light perceived by the infant; and an audio profile which initially simulates intrauterine cardiovascular and gastro-intestinal sounds and gradually transitions to normal extrauterine sounds.

43 Claims, 9 Drawing Figures

INFANT ENVIRONMENTAL TRANSITION SYSTEM

This is a continuation of application Ser. No. 131,126, filed Apr. 5, 1971, now U.S. Pat. No. 3,809,065.

BACKGROUND OF THE INVENTION

Animals have the capability of adapting to many and various environmental conditions; the limitation of adaptation depends mainly on the animals' absolute physilogical limitations and the rate of environmental change of adaptive pressure to which the animal is subjected. Successful adaptation to a new environment is frequently based on adequate previous learning or adaptation to environmental change. There are, inevitably, limits to the rate at which any animal can cope with environmental change. Exceeding these limits can result in a physiological breakdown (illness or death) and/or behavioristic reactions (inhibition or fear learning), which may program large areas of the infant's subsequent life. The adaptive capacity or capability can apparently always be extended or increased by an incremental or programmed chance in the environment which is within the adaptive limits of the animal.

The most difficult transition that a mammal is required to make in his lifetime would appear to be the change from the intrauterine environment to the extrauterine environment at birth. Not only is every element of the infant's environment changed, but the effect (fear learning) is intensified because the animal has had no experience in adapting to changing environmental conditions, as the intrauterine environment is highly protected by a number of mechanisms provided by nature.

The environmental changes through which an infant must transition include:

1. Temperature

The infant is maintained at body core temperature of 98.6° and transitions to delivery room temperature of approximately 70°. These figures may be modified by an increased maternal core temperature due to labor and evaporative cooling which the wet infant endures. The thermal shock of birth transition will range between 30° and 40° F.

2. Tactile sensation

An omni present, enclosing, mild, weightless, tactile sensation is present and applied equally over 100% of the infant's body. This sensation is generated by the uterus, the amniotic sac, and the hydraulic amniotic fluid system. In extrauterine life this tactile sensation is changed to a pressure against small portions of the infant's head, trunk and legs estimated to be 15% to 20% of the body surface area. The weightlessness of counter balanced density in utero is changed to a feeling of heaviness as the infant is pressed by his own weight against a flat, comparatively hard, pad.

3. Audio

The term gravid intrauterine audio profile consists of a loud continuous din created mainly by maternal cardiovascular and gut sounds. The fluid sound transmission system present in the uterus is approximately five times as efficient as sound transmission in air. The extrauterine enviornment is strikingly different in audio patterns and in efficiency of transmission. Acoustic trauma can be induced by changing a long preconditioned sound pattern from loud to quiet equally as well as from quiet to loud.

4. Motion

The uterine enclosure moves frequently and smoothly in rolling movements about the fetus both day and night. The system is highly protective as pressures are transmitted through a hydraulic fluid equally to all portions of the infant's body. The infant is weightless and capable of free and easy movements within the container. In the extrauterine environment, the infant is pressed by his own weight, against the crib pad. His own movements are nearly impossible and the movement of the bassinet is completely foreign to anything he has experienced.

5. Light

The illumination level in the uterus is approximately zero. The infant is transitioned into an operating room illumination level of 200 to 300 foot lamberts of light energy.

Infant care, particularly immediately following birth, has evolved over the last several decades into a pattern which appears to be contrary to a healthy adaptation of the infant to its new environment. Most women in modern societies will give birth to their children in hospitals. To minimize microbiological contamination, hospital care is most often programmed for the newborn infant in such a way as to remove the infant from the mother and isolate it in a nursery. The nursery is frequently well lighted and kept at a temperature which is considerably less than the temperature the infant experiences in the intrauterine environment. In addition, the acoustic and tactile environment are grossly altered, as compared to the world the infant has known. Applicant is of the opinion that this abrupt change in the environment tends to intensify the infant's intrauterine to extrauterine transition and may create adaptive scars which affect the person's emotional and physical response to the subsequent adaptive or environmental changes throughout the remainder of his life.

The present invention has for one of its objects a method and apparatus which provides a gradual transition of an infant from its intrauterine environment to the extrauterine environment without requiring significant changes in the current method of handling and care of the infant.

Another object of the invention is to provide a new and improved infant environmental transistion system which initially simulates parameters of the environment of the near term gravid uterus as the infant perceives them through bodily senses and changing said simulated parameters to parameters simulative of the extrauterine environment at a rate within the normal or nonpathological adaptive capacity of the infant.

A further object of the present invention is to provide a new and improved infant environmental transition system which initially simulates temperature, light, tactile sensation, motion and audio profile sensed by the infant in the near term gravid uterus and gradually changes these simulative parameters to simulate the extrauterine environment to which the infant must adapt.

PREFERRED EMBODIMENT

These and other objects will become apparent to one skilled in the art in the following specification and drawings and in which.

Figure 1:
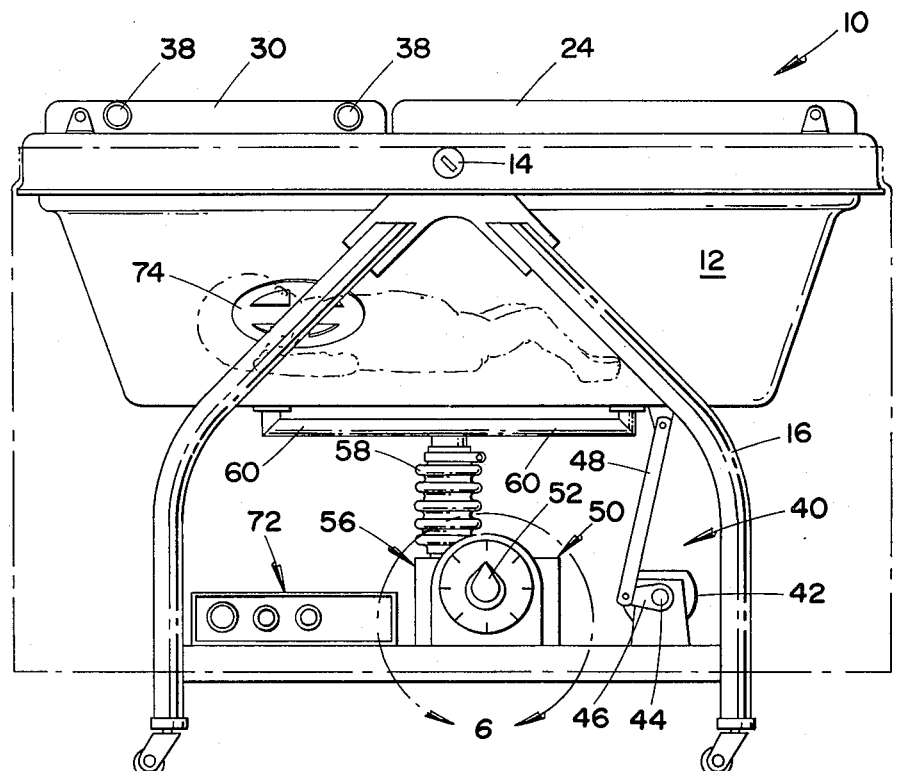
FIG. 1 is a side elevational view of the simulator according to the present invention.
Figure 2:
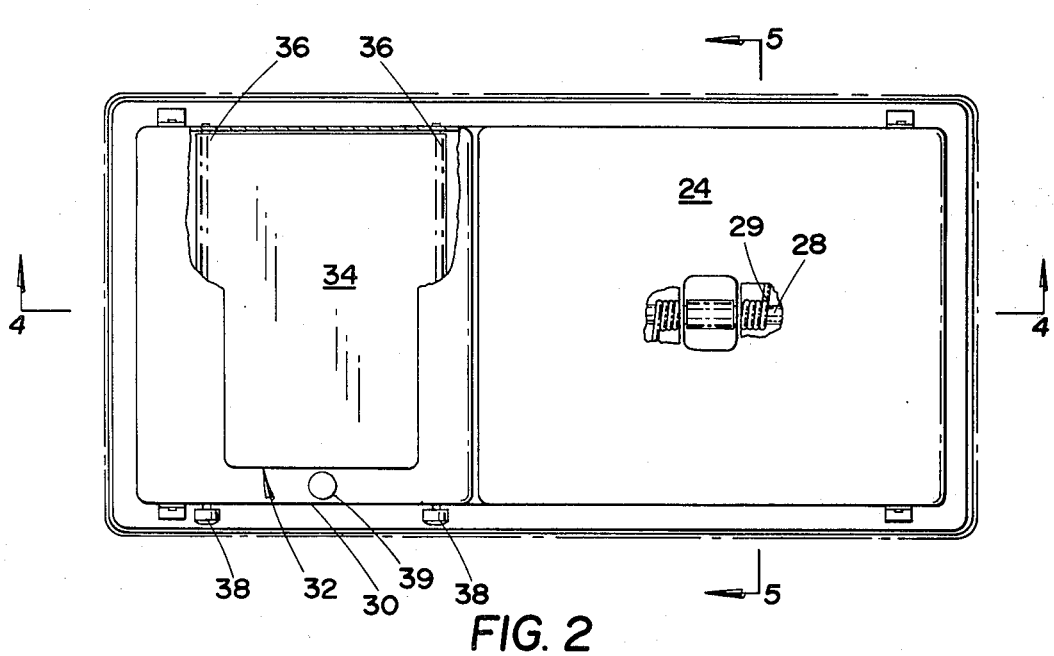
FIG. 2 is a plan view of the simulator of FIG. 1.
Figure 3:
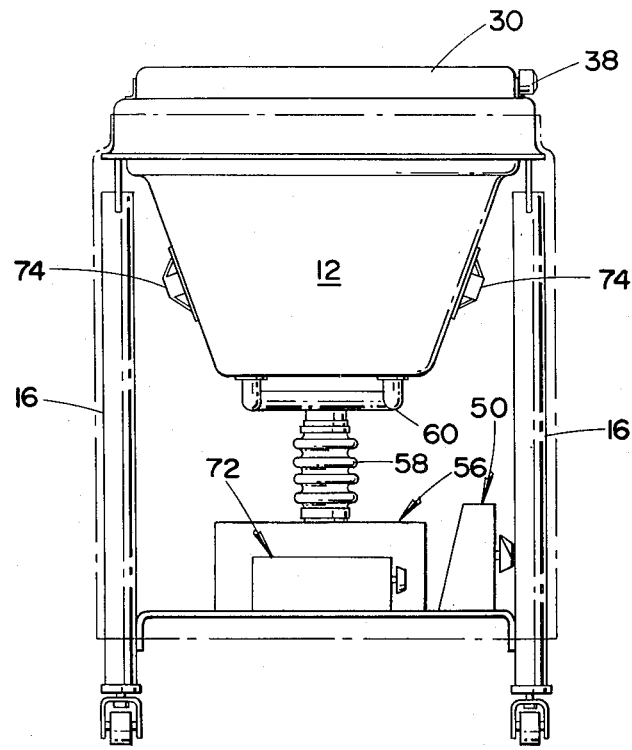
FIG. 3 is an end view of the simulator of FIG. 1.

Referring to the drawings and initially to FIG. 1, an environmental system or simulator 10 is disclosed embodying the present invention. The simulator 10 provides for a gradual controlled transition for the infant from its intrauterine environment to the extrauterine or everyday environment to reduce the adaptive shock to the infant and permit a healthy adaptation. This transition is accomplished by system 10 reproducing initially, as nealy practical, environmental parameters sensed by the infant just prior to birth such as body core temperature and humidity, audio profile, light, rocking motion, and tactile sensation. The system 10 gradually changes these parameters until the infant is exposed to parameters approximating the everyday environment.

The simulator 10 comprises a housing or container 12 adapted to receive the infant and which is supported by trunnions 14 on a frame 16. The housing 12 and frame 16 can be of various configurations as long as they contribute their respective functions to the simulator.

Figure 4:
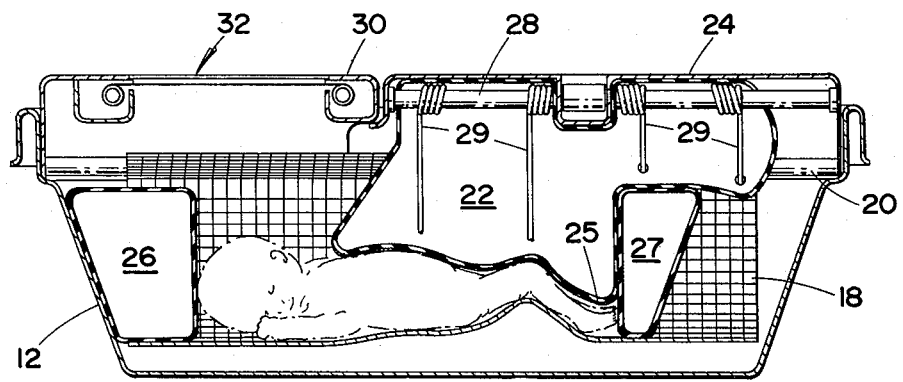
FIG. 4 is a sectional view of the simulator taken approximately along line 4—4 of FIG. 2.
Figure 5:
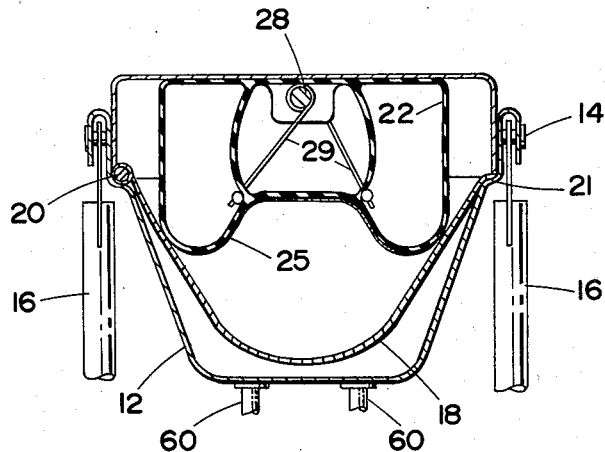
FIG. 5 is a sectional view taken approximately along line 5—5 of FIG. 2.
Figure 6:
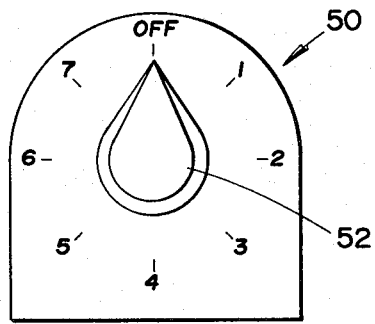
FIG. 6 is an elevational view illustrating an element of the simulator control encompassed by circle identified as 6 in FIG. 1 on an enlarged scale.

The infant is supported in housing 12 by an adjustable sling 18 (FIGS. 4 and 5). Sling 18 is preferably of net-like or skeletal construction which is flexible to conform to the infant's body like a hammock. The infant can be placed on sling 18 with or without clothing. In the later case, the waste products generated by the infant can fall into an appropriate removable tray provided in the bottom of housing 12 through openings in the sling 18 if that feature is desirable.

The net-like sling construction also permits the controlled air to circulate around the infant's body while in the housing 12. The flexibility of the sling 18 permits the sling to conform to the infant's body and thus provide the tactile sensation to which the infant is accustomed while in the intrauterine environment.

The sling 18 is dependably supported in housing 12 by a rotatable rod-like support 20 on one side and fixed at 21 along the opposite side. The rod-like support 20 can be manually rotated to gradually take up one end of the sling until eventually the sling is a flat support similar to a mattress.

The tactile sensation is further enhanced by a fabric covered low pressure pneumatic bladder 22 which is fitted to the under side of a pivoted cover 24 for the container 12. The base of the bladder may have a soft fabric layer 25 which when the bladder 22 is properly inflated exerts a very slight pressure against the infant, yet can easily be pushed away by the infant during exercise or movement. Head and foot pillows 26, 27 may be placed as shown on FIG. 4 which in combination with sling 18 and bladder 22 provide the infant with substantially encircling tactile sensation.

The bladder 22 is gradually taken up by rotating a rod 28 connected to bladder 22 by strings 29. Toward the end of the infant's stay in the simulator, the bladder 22 will be moved completely out of contact with the infant and can be removed from cover 24.

The infant is placed in and removed from the housing 12 through the pivoted cover 24. Cover 24 when raised moves bladder 22 out of the way so as not to interfere with placing or removing the infant from the simulator 10. A second pivoted cover 30 is provided and completes closure of the container 12.

When the baby is placed in sling 18 and covers 24 and 30 are closed, the simulator 10 is substantially light tight to permit good control of the light admitted to the infant. Means 32 is provided in cover 30 to control the amount of admitted light. Means 32 may include a roll of decreasingly filtered flexible window material 34. The material 34 is connected at its ends to spools 36 supported in cover 30. Spools 36 can be rotated by knobs 38 to periodically change the degree of light admitted through material 34 by rolling same from one spool 36 to the other. A window 39 in cover 30 permits display of a numeral printed on the material 34 to indicate the portion of the filter material 34 that should be exposed for a particular period of age, for example, for the week of age of the infant. The material should filter light mainly from one side so that the infant can be easily viewed from outside the housing 12.

The simulator 10 incorporates means 40 (FIG. 1) for imparting a rocking motion to the housing 12 causing the housing 12 to pivot around trunnions 14. The motion imparting means 40 includes an electrical motor 42 which drives an output shaft 44 which is drivingly connected to the housing 12 through linkage 46, 48. When shaft 44 rotates in a clockwise direction as viewed in FIG. 1, motion is imparted to housing 12 through the links 46, 48 causing the housing 12 to go through a gentle rocking sequence. The motor 42 is controlled by control means 50.

Control means 50 is a timed control mechanism which is setable to close a circuit (not shown) periodically to impart the rocking motion according to a desired sequence. The control means 50 provides additional control functions which will be explained more fully hereafter. For purposes of controlling the motion imparting means 40, a selector 52 is set according to the age of the infant. When so set, control 50 will during the early weeks of birth effect actuation of motor 42 more frequently than at the end of the period of confinement. The selector may, for example, be advanced once each week, and the new setting will reduce the frequency of the rocking motion of housing 12 until finally there will be no rocking of the housing 12.

The air in housing 12 is initially controlled to provide a warm, moist environment similar in temperature to that experienced by the infant in the embryonic sac. Since the housing 12 is partially closed to ambient air, an air control means 56 is provided for generating and directing a source of air at proper temperature and humidity into the bottom of housing 12 through a flexible hose 58 and manifold 60. The control means 56 can be any satisfactory commercially available unit which has the capability of varying the temperature and relative humidity of the air. An air cooler may be incorporated for very hot climates.

The integrated controller 50 also controls the temperature and humidity of the air directed into the housing 12 through an electrical circuit (not shown). The air circulates within the housing 12 and is exhausted through suitable leakage designed into the housing 12. The temperature and humidity of the air is gradually reduced so that the last week the infant is in the simulator 10 the air will be approximately at or about ambient room conditions.

Figure 7:
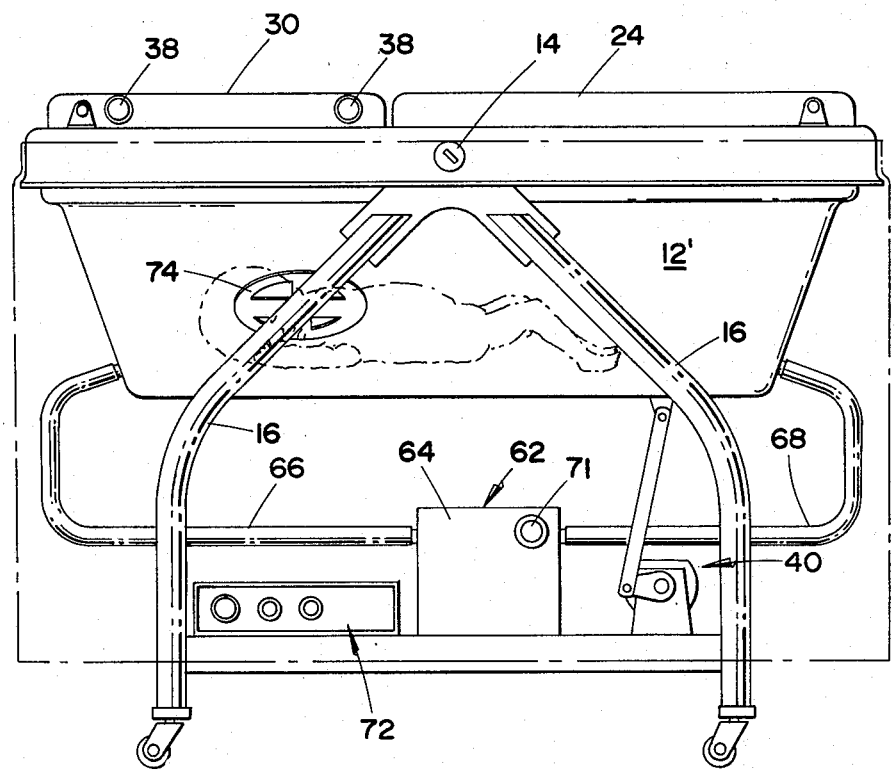
FIG. 7 is a view of the simulator similar to FIG. 1 but showing a modification thereto.
Figure 8:
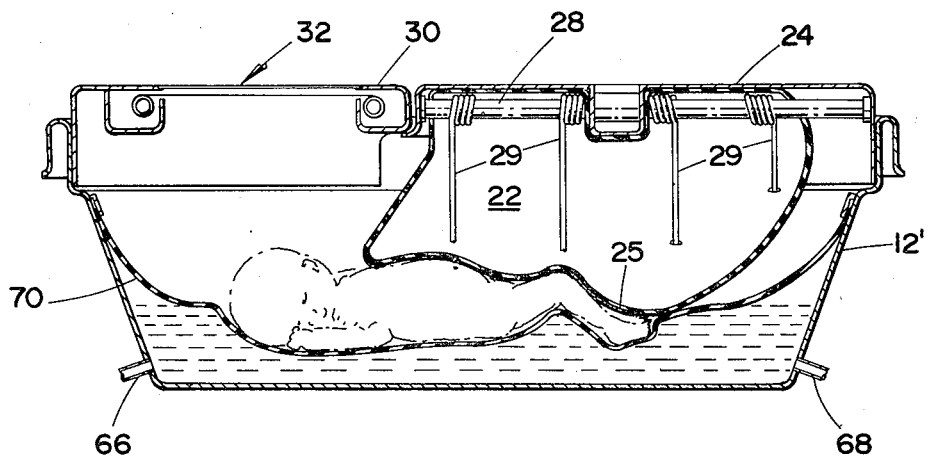
FIG. 8 is a view similar to FIG. 4 but further illustrates the modification of FIG. 7.
Figure 9:
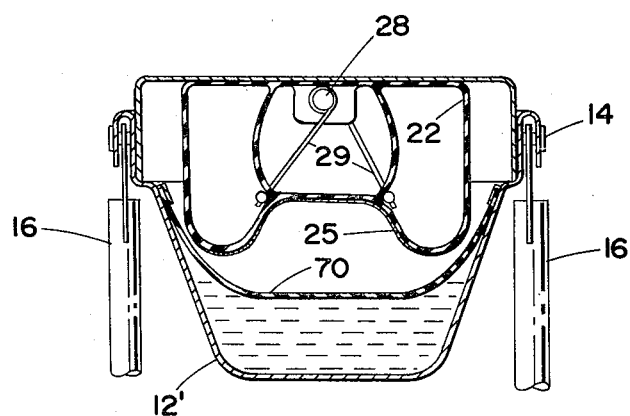
FIG. 9 is a view similar to FIG. 5 showing still further details of the modification disclosed in FIGS. 7 and 8.

FIGS. 7, 8, and 9 disclose a modified control means indicated generally as 62. Control means 62 includes a basic heating unit 64 which is controllable to heat and pumps water of varying temperatures through conduits 66 to the housing 12'. The control means 62 heats the water to a particular temperature and pumps through conduit 66 to a modified housing 12' best illustrated in FIG. 8. The water flows into the housing 12' and out the outlet 68 where it is returned to the pumping and heating unit 64.

The modified housing 12' includes a rubber sheet or the like 70 which forms a water tight barrier between the bottom of the housing 12' and the upper portion thereof into which the infant is placed. The water temperature is controlled initially at a higher temperature and gradually reduced to ambient temperature by setting the control knob 72. The infant is placed on the rubber sheet 70 and the temperature of the infant is controlled by the water circulating through the housing 12'.

The simulator 10 further includes means 72 for generating acoustical energy. Means 72 may comprise a radio, tape recorder, electronic signal generator, or similar controllable sound generating device. The audio content may comprise a variety of different simulated sounds or actual recordings of the noises present in the near term pregnant uterus or other sounds such as music or house sounds which may be generated electronically, put on tape, or played from a transmitter and reproduced in the housing 12. The acoustical means 72 directs the signal to speakers 74 suitably mounted on the sides of housing 12 and which direct the sound into the interior of the housing 12. The acoustic generator 62 can be suitably supported on a shelf provided on frame 16. The sound directed to the infant, like the other environmental factors, will be gradually changed during tenancy of the infant from the intrauterine sounds to the outside world sounds under which the baby will be subjected. Later sounds can be, for example, ordinary day noises, music, etc.

The system may also incorporate an information system comprising a cardiophone or breath sensor mounted inside the simulator and connected to remote speaker or alarm signal for the mother or nurse to monitor.

It should be apparent from the foregoing that preferred embodiments of the invention provide an apparatus and method which can initially simulate near term gravid intrauterine parameters and then provide for a gradual progressive transition of the infant from intrauterine to extrauterine environment. It should be appreciated that the particular apparatus is illustrative of the preferred embodiment to provide the variable parameters but may, however, take many forms; and it is intended that the invention be restricted only by the scope of the appended claims. It should also be appreciated that further research may reveal that some sensory parameters are more important than others in which case the means to produce a specific sensation may be altered or even eliminated to keep the total device both simple and maximally effective.

Having described my invention, I claim:

1. An environmental transition system for infants operative to simulate the intrauterine environment sensed by the infant while in the uterus and gradually change the simulated intrauterine environment over a period of time to the extrauterine environment sensed by the infant after it leaves the uterus comprising: a housing for receiving said infant upon delivery having means for supporting an infant therein, first respective means for generating in said housing at least four of the sensory environmental conditions of sound, temperature, tactile sensation, light and motion as sensed by the infant in its intrauterine environment, and second respective means associated with said first respective means for gradually changing said conditions from their initial values over a period of time to values substantially equal to those of the extrauterine environment.

2. An environmental transition system for infants operative to simulate the intrauterine environment sensed by the infant while in the uterus and gradually change the simulated intrauterine environment over a period of time to the extrauterine environment sensed by the infant after it leaves the uterus comprising: a housing for receiving said infant upon delivery having means for supporting an infant therein, first respective means for generating in said housing at least three of the sensory environmental conditions of sound, temperature, tactile sensation, light, and motion as sensed by the infant in its intrauterine environment, one of which is light, and second respective means associated with said first respective means for gradually changing said conditions from their initial values over a period of time to values substantially equal to those of the extrauterine environment.

3. An environmental transition system for infants operative to simulate the intrauterine environment sensed by the infant while in the uterus and gradually change the simulated intrauterine environment over a period of time to the extrauterine environment sensed by the infant after it leaves the uterus comprising: a housing for receiving said infant upon delivery having means for supporting an infant therein, first respective means for generating in said housing at least three of the sensory environmental conditions of sound, temperature, tactile sensation, light, and motion as sensed by the infant in its intrauterine environment, one of which is sound, said sound consisting of reproduced or simulated maternal cardiovascular and gut sounds as perceived by an intrauterine infant in late pregnancy, and second respective means associated with said first respective means for gradually changing said conditions from their initial values over a period of time to values substantially equal to those of the extrauterine environment.

4. An environmental transition system for infants operative to simulate the intrauterine environment sensed by the infant while in the uterus and gradually change the simulated intrauterine environment over a period of time to the extrauterine environment sensed by the infant after it leaves the uterus comprising: a housing for receiving said infant upon delivery having means for supporting an infant therein, first respective means for generating in said housing at least three of the sensory environmental conditions of sound, temperature, tactile sensation, light, and motion as sensed by the infant in its intrauterine environment, wherein one condition is tactile sensation, said tactile sensation being defined as a resilient, formfitting surface which is adaptable to engage upper and lower portions of the infant's body, and second respective means associated with said first respective means for gradually changing said conditions from their initial values over a period of time to values substantially equal to those of the extrauterine environment.

5. An environmental transition system for infants operative to simulate the intrauterine environment sensed by the infant while in the uterus and gradually change the simulated intrauterine environment over a period of time to the extrauterine environment sensed by the infant after it leaves the uterus comprising: a housing for receiving said infant upon delivery having means for supporting an infant therein, first respective means for generating in said housing at least two of the sensory environmental conditions of sound, temperature, tactile sensation, light, and motion as sensed by the infant in its intrauterine environment, wherein one condition is tactile sensation, said tactile sensation being defined as a resilient, form fitting surface which is adaptable to engage upper and lower portions of the infant's body, and second respective means associated with first respective means for gradually changing said conditions from their initial values over a period of time to values substantially equal to those of the extrauterine environment.

6. An environmental simulator as defined in claim 5 wherein said means for supporting an infant comprises a sling supported along opposite sides thereof and means for adjusting the effective length of the sling between said support whereby said sling is gradually changed to a substantially flat supporting surface.

7. An environmental simulator as defined in claim 6 wherein said sling is made out of a mesh type material.

8. An environmental simulator as defined in claim 6 wherein said sling is made of waterproof material and said sling in the fully deployed position extends into a reservoir of waer provided in the bottom portion of the housing.

9. An environmental simulator as defined in claim 8 further including means for circulating and controlling the temperature of said water in said reservoir.

10. An environmental simulator as defined in claim 5 further comprising inflatable means depending from the upper portion of said housing for inflation into a position to contact the upper side of an infant when an infant is supported in said housing.

11. An environmental simulator as defined in claim 10 further including means for selectively moving said inflatable means out of contact with the infant.

12. An environmental transition system for infants operative to simulate the intrauterine environment sensed by the infant while in the uterus and gradually change the simulated intrauterine environment over a period of time to the extrauterine environment sensed by the infant after it leaves the uterus comprising: a housing for receiving said infant upon delivery having means for supporting an infant therein, first respective means for generating in said housing at least two of the sensory environmental conditions of sound, temperature, tactile sensation, light, and motion as sensed by the infant in its intrauterine environment, wherein one condition is light, said light including means to control ambient light entering the housing, and second respective means associated with said first respective means for gradually changing said conditions from their initial values over a period of time to values substantially equal to those of the extrauterine environment.

13. An environmental simulator as defined in claim 12 wherein said means for generating environmental conditions of light in said housing further includes light filtering material which has varying degrees of opacity and means for supporting said material so that selected portions thereof can be positioned to admit varying amounts of light to the infant in said housing.

14. An environmental transition system for infants operative to simulate the intrauterine environment sensed by the infant while in the uterus and gradually change the simulated intrauterine environment over a period of time to the extrauterine environment sensed by the infant after it leaves the uterus comprising: a housing for receiving said infant upon delivery having means for supporting an infant therein, first respective means for generating in said housing at least two of the sensory environmental conditions of sound, temperature, tactile sensation, light, and motion as sensed by the infant in its intrauterine environment, wherein one condition is sound, said sound consisting of reproduced or simulated maternal cardiovascular and gut sounds as perceived by an intrauterine infant in late pregnancy, and second respective means associated with said first respective means for gradually changing said conditions from their initial values over a period of time to values substantially equal to those of the extrauterine environment.

15. An environmental transition system for infants operative to simulate the intrauterine environment as sensed by the infant while in the uterus comprising: a housing for receiving said infant upon delivery having means for generating in said housing at least four of the sensory environmental conditions of sound, temperature, tactile sensation, light and motion as sensed by the infant in its intrauterine environment, and second respective means associated with said first respective means for controlling change in the intrauterine-extrauterine transition environment.

16. The environmental transition system of claim 15 including means for gradually reducing over a period of time the exposure of said infant placed in the environmental transition system to said simulated intrauterine sensory environmental conditions to condition the infant to the extrauterine environment at an optimal rate.

17. The environmental transition system of claim 15 including means to vary at least one of either the intensity of said exposure or the time period of said exposure.

18. An environmental transition system for infants operative to simulate the intrauterine environment as sensed by the infant while in the uterus comprising: a housing for receiving said infant upon delivery having means for generating in said housing at least three of the sensory environmental conditions of sound, temperature, tactile sensation, light, and motion as sensed by the infant in its intrauterine environment, one of which is light, and second respective means associated with said first respective means for controlling change in the intrauterine-extrauterine transition environment.

19. The environmental transition system of claim 18 including means for gradually reducing over a period of time the exposure of said infant placed in the environmental transition system to said simulated intrauterine sensory environmental conditions to condition the infant to the extrauterine environment at an optimal rate.

20. The environmental transition system of claim 19 including means to vary at least one of either the intensity of said exposure or the time period of said exposure.

21. An environmental transition system for infants operative to simulate the intrauterine environment as sensed by the infant while in the uterus comprising: a housing for receiving said infant upon delivery having means for generating in said housing at least three of the sensory environmental conditions of sound, temperature, tactile sensation, light, and motion as sensed by the infant in its intrauterine environment, one of which is sound, said sound consisting of reproduced or simulated maternal cardiovascular and gut sounds as perceived by an intrauterine infant in late pregnancy, and second respective means associated with said first respective means for controlling change in the intrauterine-extrauterine transition environment.

22. The environmental transition system of claim 21 including means for gradually reducing over a period of time the exposure of said infant placed in the environmental transition system to said simulated intrauterine sensory environmental conditions to condition the infant to the extrauterine environment at an optimal rate.

23. The environmental transistion system of claim 22 including means to vary a least one of either the intensity of said exposure or the time period of said exposure.

24. An environmental transition system for infants operative to simulate the intrauterine environment as sensed by the infant while in the uterus comprising: a housing for receiving said infant upon delivery having means for generating in said housing at least three of the sensory environmental conditions of sound, temperature, tactile sensation, light, and motion as sensed by the infant in its intrauterine environment, wherein one condition is tactile sensation, said tactile sensation being defined as a resilient, form fitting surface which is adaptable to engage upper and lower portions of the infant's body, and second respective means associated with said first respective means for controlling change in the intrauterine-extrauterine transition environment.

25. The environmental transition system of claim 24 including means for gradually reducing over a period of time the exposure of said infant placed in the environmental transition system to said simulated intrauterine sensory environmental conditions to condition the infant to the extrauterine environment at an optimal rate.

26. The environmental transition system of claim 25 includng means to vary at least one of either the intensity of said exposure or the time period of said exposure.

27. An environmental transition system for infants operative to simulate the intrauterine environment as sensed by the infant while in the uterus comprising: a housing for receiving said infant upon delivery having means for generating in said housing at least two of the sensory environmental conditions of sound, temperature, tactile sensation, light, and motion as sensed by the infant in its intrauterine environment, wherein one condition is tactile sensation, said tactile sensation being defined as a resilient, form fitting surface which is adaptable to engage upper and lower portions of the infant's body, and second respective means associated with said first respective means for controlling change in the intrauterine-extrauterine transition environment.

28. The environmental transition system of claim 27 including means for gradually reducing over a period of time the exposure of said infant placed in the environmental transition system to said simulated intrauterine sensory environmental conditions to condition the infant to the extrauterine environment at an optimal rate.

29. The environmental transition system of claim 28 including means to vary at least one of either the intensity of said exposure or the time period of said exposure.

30. An environmental transition system for infants operative to simulate the intrauterine environment as sensed by the infant while in the uterus comprising: a housing for receiving said infant upon delivery having means for generating in said housing at least two of the sensory environmental conditions of sound, temperature, tactile sensation, light, and motion as sensed by the infant in its intrauterine environment, wherein one condition is light, said light including means to control ambient light entering the housing, and second respective means associated with said first respective means for controlling change in the intrauterine-extrauterine transition environment.

31. The environmental transition system of claim 30 including means for gradually reducing over a period of time the exposure of said infant placed in the environmental transition system to said simulated intrauterine sensory environmental conditions to condition the infant to the extrauterine environment at an optimal rate.

32. The environmental transition system of claim 31 including means to vary at least one of either the intensity of said exposure or the time period of said exposure.

33. An environmental transition system for infants operative to simulate the intrauterine environment as sensed by the infant while in the uterus comprising: a housing for receiving said infant upon delivery having means for generating in said housing at least two of the sensory environmental conditions of sound, temperature, tactile sensation, light, and motion as sensed by the infant in its intrauterine environment, wherein one condition is sound, said sound consisting of reproduced or simulated maternal cardiovascular and gut sounds as perceived by an intrauterine infant in late pregnancy, and second respective means associated with said first respective means for controlling change in the intrauterine-extrauterine transition environment.

34. The environmental transition system of claim 33 including means for gradually reducing over a period of time the exposure of said infant placed in the environmental transition system to said simulated intrauterine sensory environmental conditions to condition the infant to the extrauterine environment at an optimal rate.

35. The environmental transition system of claim 34 including means to vary at least one of either the intensity of said exposure or the time period of said exposure.

36. The method of transitioning an infant from intrauterine to extrauterine life by retaining the infant for a period of time under an optimum number of the conditions of sound, temperature, light, motion and tactile sensation simulating those same environmental conditions as sensed by the infant in the intrauterine environment, the method comprising:
  a. providing a housing of internal size to receive and support the infant after delivery;
  b. providing said housing with at least three of said sensory environmental conditions of sound, temperature, light, motion and tactile sensation;
  c. transferring said infant to said housing after delivery; and
  d. gradually conditioning said infant in said housing from the intrauterine to the extrauterine environment by gradually reducing over a period of time the time period or intensity or both to which said infant is exposed to said simulated intrauterine environmental conditions in said housing.

37. The method of claim 36 in which one of said three sensory environmental conditions is light.

38. The method of claim 36 in which one of said three sensory environmental conditions is sound, said sound consisting of simulated maternal cardiovascular and gut sounds as perceived by a intrauterine infant in late pregnancy.

39. The method of claim 36 in which one of said three sensory environmental conditions is tactile sensation defined as a resilient, form fitting surface which is adaptable to engage upper and lower portions of the infant's body.

40. A method for conditioning an infant from the conditions of sound, temperature, tactile sensation, light and motion sensed by the infant in its intrauterine environment to those existing in its extrauterine environment, comprising the steps of:
  a. providing a housing to receive the infant upon delivery having means for adjusting its effective internal area contacting the infant to provide substantially constant tactile sensation about the infant's body;
  b. initially providing said housing with at least two of the environmental conditions of sound, temperature, tactile sensation, light, as defined in (a) and motion of an intensity equal to that sensed by the infant in its intrauterine environment as indicated by the infant's autonomic nervous system responses;
  c. transferring the infant to said housing upon delivery; and thereafter
  d. gradually over a period of time changing the intensity of at least two of said conditions in said housing to the intensity of said two conditions in the extrauterine environment to which the infant must adjust.

41. The method of transitioning an infant from intrauterine to extrauterine life by retaining the infant for a period of time under an optimum number of conditions of sound, temperature, light, motion and tactile sensations simulating those same environmental conditions as sensed by the infant in the intrauterine environment, the method comprising:
  a. providing a housing of internal size to receive and support the infant after delivery;
  b. providing said housing with at least two of said sensory environmental conditions wherein one of said conditions is tactile sensation defined as a resilient, form fitting surface which is adaptable to engage upper and lower portions of the infant's body;
  c. transferring said infant to said housing after delivery; and
  d. gradually conditioning said infant in said housing from the intrauterine to the extrauterine environment by gradually reducing over a period of time the time period or intensity or both to which said infant is exposed to said simulated intrauterine environmental conditions in said housing.

42. The method of transitioning an infant from intrauterine to extrauterine life by retaining the infant for a period of time under an optimum number of the conditions of sound, temperature, light, motion and tactile sensation simulating those same environmental conditions as sensed by the infant in the intrauterine environment, the method comprising:
  a. providing a housing of internal size to receive and support the infant after delivery;
  b. providing said housing with at least two of said sensory environmental conditions, one of which is light, and including means to control ambient light entering the housing;
  c. transferring said infant to said housing after delivery; and
  d. gradually conditioning said infant in said housing from the intrauterine to the extrauterine environment by gradually reducing over a period of time the time period or intensity or both to which said infant is exposed to simulated intrauterine environmental conditions in said housing.

43. The method of transitioning an infant from intrauterine to extrauterine life by retaining the infant for a period of time under an optimum number of the conditions of sound, temperature, light, motion and tactile sensation simulating those same environmental conditions as sensed by the infant in the intrauterine environment, the method comprising:
  a. providing a housing of internal size to receive and support the infant after delivery;
  b. providing said housing with at least two of said sensory environmental conditions, wherein one of said conditions is sound consisting of reproduced or simulated maternal cardiovascular and gut sounds as perceived by an intrauterine infant in late pregnancy;
  c. transferring said infant to said housing after delivery; and
  d. gradually conditioning said infant in said housing from the intrauterine to the extrauterine environment by gradually reducing over a period of time the time period or intensity or both to which said infant is exposed to said simulated intrauterine environmental conditions in said housing.

* * * * *